United States Patent [19]

Tentor

[11] 4,304,122
[45] Dec. 8, 1981

[54] DEEP WELL SIMULATOR

[75] Inventor: Sergio Tentor, Newark, Del.

[73] Assignee: E. I. Du Pont de Nemours and Company, Wilmington, Del.

[21] Appl. No.: 147,179

[22] Filed: May 6, 1980

[51] Int. Cl.³ .......................................... G01N 15/08
[52] U.S. Cl. ........................................ 73/38; 73/153; 73/432 SD
[58] Field of Search .................... 73/38, 153, 432 SD

[56] References Cited

U.S. PATENT DOCUMENTS

| | | |
|---|---|---|
| 2,345,935 | 4/1944 | Hassler . |
| 2,390,252 | 12/1945 | Hayward . |
| 2,498,198 | 2/1950 | Beeson . |
| 2,737,804 | 3/1956 | Herzog et al. ............ 73/38 |
| 3,018,660 | 1/1962 | Schmid ................. 73/153 |
| 3,073,149 | 1/1963 | Mongan ................. 73/38 |
| 3,420,093 | 1/1969 | Collins .................. 73/38 |

Primary Examiner—Jerry W. Myracle

[57] ABSTRACT

An apparatus for measuring the permeability of solids at any given condition of pressure and temperature and flow rate, the control of pressure being achieved without a valve by using capillary tubing containing an oil. The apparatus is capable of operating at constant pressure automatically for long periods of time and a method for using the apparatus to measure permeability of a solid at constant flow rate and constant pressure.

10 Claims, 4 Drawing Figures

DEEP WELL SIMULATOR

DESCRIPTION OF THE INVENTION

1. Field of the Invention

This invention relates to a method of measuring permeability and changes in permeability of a solid substance and the apparatus involved. More specifically, this invention relates to a method of measuring permeability and changes in permeability of a solid material that may be present beneath the earth's surface by using an apparatus that permits the duplication of any desired temperature, pressure and flow rate.

2. Background of the Invention

The study of the movement of fluids through geologic deposits of porous materials is becoming increasingly significant due to, among other things, the increasing need to dispose of waste liquids and to improve the existing disposal of said liquids by methods that avoid injury to people or environment. There is therefore a need for a method as well as an apparatus that can be used to simulate the injection of fluids underground at actual conditions of temperature, pressure and flow rate. This is done to determine permeability and permeability changes of any geologic deposits since permeability largely characterizes the ability of these geologic deposits to accept wastes and also is indicative of chemical interaction. The determination of permeability is important in the study of fluid movements beneath the earth's surface.

Apparatuses intended for short-term tests for determining earth core permeability to liquids where corrosion or chemical reaction of the liquid and earth core are not a factor, e.g., for determining the suitability of earth strata for producing petroleum are disclosed in U.S. Pat. Nos. 2,390,252; 2,498,198; 2,737,804; 3,018,660; 3,073,149 and 3,420,093. These prior art apparatuses are usually operated for relatively short time periods and are operated manually in terms of adjusting or maintaining temperatures, pressures, flow rates and the like. Thus, such apparatuses are not suited for long-term tests which may run up to e.g., 167 hours.

In those instances where the core must be maintained at an elevated temperature to simulate actual conditions, apparatuses of the prior art, however, allow the fluid being pumped to the test core to be heated by the apparatus before it reaches the core to be tested. With fluids whose compositions are unstable at elevated temperatures, this procedure causes reactions to occur outside the core to be tested. There are no provisions in the prior art for a cooling means at the entrance to the core test apparatus which will maintain the fluid below the decomposition temperature until it has contacted the core.

Apparatuses of the prior art do not provide a means for automatically maintaining the test pressure constant at the pressures described herein without change or drift in the core test pressure and without the continual monitoring and interaction by an operator as, e.g., by adjusting a throttling valve or the like.

There is a need for an apparatus resistant to corrosive materials with automatic controls and continuous recording means for all parameters for longterm tests that would provide high precision in terms of maintaining pressures and flow rates throughout a long test run.

SUMMARY OF THE INVENTION

Now an apparatus has been constructed that permits constant pressure control at the exit of a solid being tested, without the use of a valve, with constant flow of test fluid and temperature control of the test fluid enroute to the solid being tested for permeability.

In accordance with the invention an apparatus has been discovered that simulates the underground conditions that may exist for any given geologic formation with respect to liquids injected into such formation. The apparatus uses titanium or polymeric parts where there is exposure to test fluids, uses automatic controls for maintaining a constant temperature of a test core from a geologic formation, uses a precise positive displacement pump to maintain a given constant flow rate irrespective of system pressure and uses a pressure letdown system for maintaining a constant pressure at the discharge side of the core that comprises a small diameter capillary tube in which flowing oil produces a pressure differential which may be controlled automatically by controlling the viscosity of the oil. The pressure letdown control is accomplished by monitoring the upstream pressure of the capillary with a transducer which is connected to a control device which varies heat input to the capillary tube by means of an electric resistance heater. Reducing the viscosity of the oil with heat permits controlling the pressure in the capillary tube.

Accordingly, an apparatus has been discovered for determining the permeability and changes in permeability of a solid to fluids as a function of time, e.g., cores taken from an underground geological formation, at particular conditions of temperature and pressure and flow rate, e.g., conditions present in the underground formation, said apparatus comprising a precision plunger-type pump, means for controlling the flow rate of liquid from the pump, a fluid reservoir housing a movable piston that divides the interior of the reservoir into two sides, a fluid side and a test fluid side, said pump connected to the fluid side of the fluid reservoir to permit said piston to be actuated by the fluid pressure exerted on the movable piston of the reservoir by the pump, a solid or core holder, the test fluid side connected to an inlet connection of the core holder, a heater adjacent to the core holder to maintain a core in the core holder at any temperature and preferably a means for monitoring and recording said temperature, a differential pressure transducer, the transducer is connected to the entrance and exit means to and from the core holder to measure and record differential pressure continuously as a function of time, a receiver with a movable piston housed therein that divides the interior of the receiver into two sides, a test fluid side and an oil side, means for passage of the test fluid from the reservoir to the inlet of the core holder, means for passage of the test fluid from the exit of the core holder to the test fluid side of the receiver, a pressure transducer, a pressure letdown capillary connected through the pressure transducer to the oil side of the receiver, a heater adjacent to the pressure letdown capillary for heating the oil in the capillary, means connected to said pressure transducer and said heater for controlling the pressure on the oil side of the receiver, by controlling the heat provided by the heater to permit a constant pressure downstream of the core holder, by providing a controlled pressure to the receiver piston to control the exit pressure of the fluid from the core holder. Preferably the present apparatus also includes a cooling manifold and means for controlling the temperature of the test fluid to prevent heat-up of the test fluid until it has entered the core.

The present invention also involves a method for measuring the permeability of a confined solid at a pressure and at a temperature and at flow rates that are encountered in nature comprising:

(1) Pumping test fluid through a core confined in said apparatus at a substantially constant flow rate;

(2) maintaining the test fluid below the fluid's decomposition temperature until it enters the core;

(3) maintaining a constant pressure of the flowing test fluid at a point in a channel downstream of the solid;

(4) varying the viscosity of the oil by controlled application of heat so as to maintain the constant pressure of (3); and (5) measuring the $\Delta P$ across the solid.

The letdown capillary tubing carrying oil has a preselected dimension of diameter and length of a size that will result, with channel and oil at ambient temperature, in a pressure downstream of the core than is greater than that desired for testing thereby requiring at least some sensible heat input to the channel and to the oil for operation at a desired pressure level.

The apparatus of the present invention can be further described by referring to the Figures.

Figure 1:
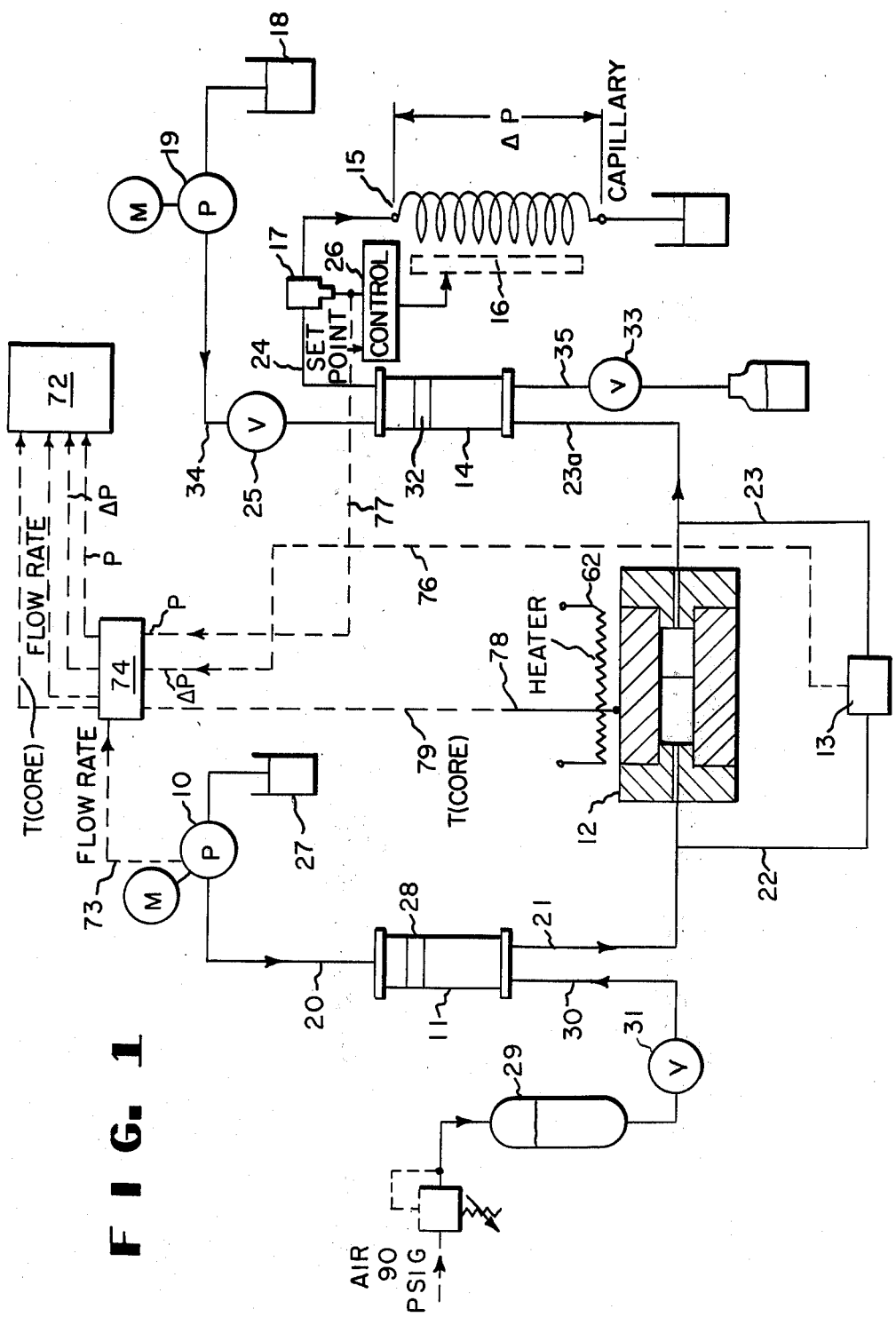
FIG. 1 is a schematic diagram of the permeability test apparatus of the present invention showing the principal parts of the apparatus including controls and their interconnections.

Referring now to FIG. 1, the apparatus employed in the present invention generally comprises a precision plunger-type pump 10 and a fluid reservoir 11 connected by a tube 20, a solid holder 12 supplied with fluid from the reservoir 11 by a tube 21, a differential pressure transducer 13 connected to the respective ends of the solid holder 12 by tubes 22 and 23, a receiver 14 connected to the outlet end of the solid holder 12 by means of a tube 23a and a pressure let-down capillary 15 with its heater 16 which is connected to the upper end of the receiver 14 by tube 24 which latter has a pressure transducer 17. Means for supplying Silicone ® oil to the receiver 14 include a sump 18, a gear pump 19 and a manually operable valve 25. Control and recording devices are also used as described below.

The plunger pump may be driven at different speeds and is used to pump water at a rate of 6–600 ml/hr at pressures up to about 6000 psi from a sump 27 to the upper end of fluid reservoir 11.

For any given test of a solid, however, it is important that the flow rate of the water and the test fluid be known and be maintained constant. Pump flow rate is inferred from pump speed which is monitored by means of a conventional revolution counter, internal to the pump, (not shown) connected via line 73 to an indicating and signal conditioning device 74 which, in turn, sends signals to a strip chart recorder 72 where the flow rate is recorded and it is checked by measuring the loss in water of sump 27 over a given time interval.

The fluid reservoir 11 is made of titanium, so as to resist corrosion, and generally comprises a tubular body within which is a "floating" piston 28, made of a copolymer of tetrafluoroethylene, ethylene and hexafluoroacetone sold by E. I. du Pont de Nemours and Company as Tefzel ® which carries an O-ring seal. Except for tube connections, the ends of the reservoir 11 are closed by means of screwed covers. The lower end of the reservoir is adapted to be charged with a test fluid (e.g., iron chloride solution) by means of a closed tank 29 arranged to be pressurized with air at about 90 psig and joined to the lower end of reservoir 11 by means of tube 30 via manually operated valve 31. Charging of the reservoir 11 is carried out with pump 10 "off" and drives floating piston 28 "up".

The differential pressure transducer 13 is of the capacitance type may be one made by Rosemount, Model No. 1151HP. The output of the differential pressure transducer 13 is connected via line 76 to the indicating and signal conditioning device 74 and, in turn, to strip chart recorder 72 where the differential pressure ($\Delta P$) across a test core is recorded.

The receiver 14 is made of titanium and has a floating piston 32 made of the aforesaid Tefzel ® being substantially identical in design to fluid reservoir 11. The receiver 14 receives effluent from core holder 12, "under" piston 32, and is arranged to be drained via tube 35 and manually operable valve 33 to remove "spent" or processed test fluid. The upper end of receiver 14 "above" piston 32 is completely filled with Silicone ® oil supplied by gear pump 19 via tube 34 and manually operable valve 25. When the apparatus is in operation, the gear pump 19 is isolated from the system by closing manual valve 25.

The pressure transducer 17 in tube 24 is of the strain gage type, made by Sensotec, Inc., Model No. A-205. This is connected to a control device 26 which modulates the electrical energy supply to a heater 16 as further described below. The pressure transducer 17 is also connected via line 77 to the indicating and signal conditioning device 74 the output of which goes to recorder 72 thus recording the pressure downstream of the test solid and upstream of the capillary 15, e.g., as controlled by control 26.

Sump 18 is arranged to supply Silicone ® oil to gear pump 19 which supplies oil under pressure (e.g., 2000 psi) to the "upper" end of receiver 14 as described above. The use of other oils that can permit constant pressure control are within the scope of the present invention.

The tubes 21, 22, 23, 23a, 30 and 35 are made of titanium to resist the corrosive effect of the test fluid; the tubes 20, 24 and 34 are made of stainless steel since they only carry water or Silicone ® oil. Valves 31 and 33 are also made of titanium and the remaining ones of stainless steel.

Figure 2:
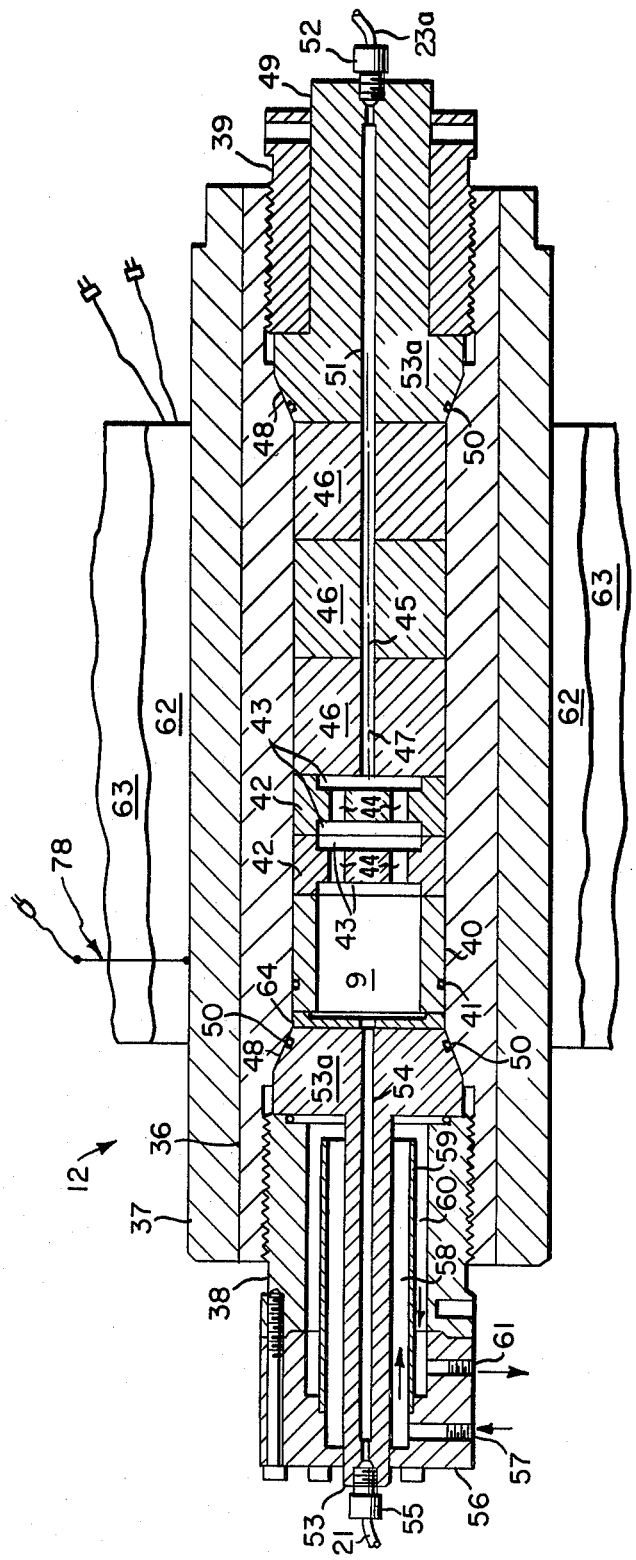
FIG. 2 is a longitudinal cross-section of a solid holder of the present invention.

Referring now to FIG. 2, the solid holder 12, also referred to as a core holder, generally comprises a titanium tube 36 in a tight-fitting steel jacket 37 which is surrounded by an electric heating jacket 62 and thermal insulation 63; the tube 36 has an internal screw thread at both ends to receive hollow steel screws 38 and 39 which serve to retain the internal parts indicated in FIG. 2, namely parts 49 and 53. A permeable core 9, removed from the earth by drilling, is enclosed in a molded epoxy resin jacket 40 which surrounds the core 9 but does not cover its ends and the epoxy resin jacket is provided with an annular groove for receiving O-ring seal 41.

On the right or downstream end of the jacketed core 9 are two traps 42 comprising titanium discs with machined recesses 43 at each end; the discs each have four equally spaced holes 44 parallel to the central axis 45 of the core holder 12 which provide flow passages for fluid. The velocity of the test fluid flowing from core 9 through successive recesses 43 and holes 44 is sufficiently low that any particulate matter carried by the test fluid will settle out in the recesses 43. Additionally, the traps 42 are rotated so that the holes 44 are not coaxial thus presenting a tortuous path to solids in the test fluid thus aiding in their settling in 43. Immediately downstream of the second trap 42 can be any number (three shown) of spacers 46 used optionally depending on the axial length of the core 9 being tested. In one embodiment the core 9 and the spacers 46 are each two inches long, thus, test cores having different lengths, e.g., 2, 4, 6 and 8 inches, can be used. The core diameter used in the present apparatus is 1.75 inches before being cast in epoxy and 2½ inches in diameter after being cast in epoxy. The spacers all have a central passage 47 for test fluid to flow through.

Inside each end of the core holder 12 the titanium tube 36 has conical seats 48 immediately inboard of the internal screw threads. On the right or outlet end a thick walled titanium tube 49 is retained by hollow screw 39 and has a shank which passes through the screw; a mushroom head with a conical exterior surface 53a mates with the conical seat 48 in tube 36; an O-ring 50 effects a seal. The tube 49 has a central flow passage 51 along axis 45 which terminates in a threaded hole occupied by a tube fitting 52 for connecting tube 23a.

On the left or inlet end of core holder 12 a mushroom headed inlet tube 53 with a conical surface (53a) and an O-ring seal 50 is seated inside tube 36 by means of hollow screw 38. A flow passage 54 extends along the axis and has a threaded portion at the left occupied by tube fitting 55 for tube 21. An important and novel feature of the inlet tube 53 is a cooling jacket 56 having a water inlet 57 to an annular space 58 which extends along the entire length of the inlet tube 53 except for the headed portion; a thin wall tube 59 provides an outer wall for the annulus 58 as well as an inner wall for an annular return passage 60 to a water outlet 61.

The electric heating jacket 62 can maintain substantially the entire core holder assembly at a high temperature up to 212° F. by reason of intimate contact between the conical head 53a of inlet tube 53 and the mating conical seat 48 of titanium tube 36 the head 53a likewise becomes heated; however, left portion of tube 53 inside annular space 58 is maintained at a relatively low temperature by the cooling water entering inlet 57. Test fluid flowing through passage 54 does not become appreciably heated until it reaches the region near the test core 9, thus any components of the test fluid which may precipitate out of solution at elevated temperatures do not do so until the fluid penetrates the test core, as intended. The temperature of the entire core assembly and therefore the core is monitored by thermocouple 78 which via line 79 is connected to the indicating and signal conditioning device 74 and, in turn, to strip chart recorder 72 where the temperature is recorded.

On the right end of conical head 53a is a Teflon ® washer 64 having a central hole and a shallow recess facing the end of test core 9; the recess serves to distribute test fluid uniformly across the end surface of core 9 radially and axially. The Teflon ® washer 64 also serves as a thermal insulator.

Figure 3:
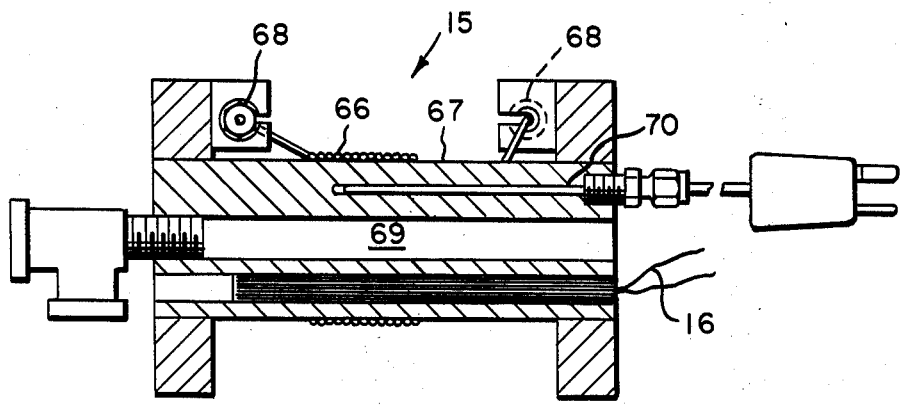
FIG. 3 is a longitudinal cross-section of the pressure let-down capillary of the present invention including a heating means.
Figure 4:
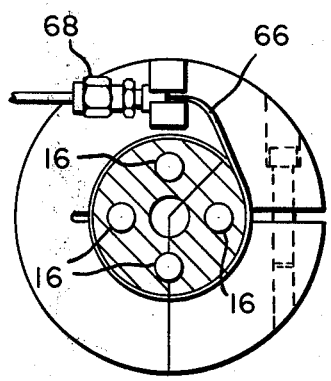
FIG. 4 is a cross-sectional view of the apparatus of FIG. 3.

Referring now to FIGS. 3 and 4, an important and novel part of the apparatus is pressure letdown capillary 15 and heaters 16. The pressure letdown comprises a small diameter stainless steel capillary tube 66 (e.g., 0.062 inch O.D. by 0.007 inch I.D.) wrapped in a single helical layer, coil-to-coil about a massive block of copper 67, circular in cross-section, the tubing having a length which is selected to generate, in the present case, about a 5000 psi pressure drop at a preselected flow rate using Silicone ® oil. The capillary length, however, can be whatever length that will generate the pressures indicated herein. Flanges at each end of the copper block serve to hold the respective ends of the capillary tubing 66 as well as conventional tube fittings 68.

A central hole 69 in the copper block 67 permits water or forced air cooling of the pressure letdown apparatus, if desired. Another hole in block 67 is occupied by a commercial thermocouple 70 which is connected to a temperature indicator (not shown). With the copper block, parallel to the central hole 69, are four smaller diameter holes, equally spaced, each of which is occupied by a 200-watt electrical cartridge heater 16. Electrical energy is supplied to the heaters as shown in FIG. 1 via a control 26 which is also connected to a pressure transducer 17 in tube 24. The pressure at the exit of the core of the present apparatus and method may be controlled automatically generally at pressures up to 40,000 psig. However, the present apparatus may be most useful at pressures of 3,000–40,000 psig. Most of the simulations required pressures of 3,000–10,000 psig.

It will be realized that the capillary tube diameter and length determine pressure drop with a given fluid at a given flow rate; the tube dimensions may be selected with the aid of the expression:

$$\Delta P = \frac{32 \mu V L}{D^2}$$

where
$\Delta P$ = pressure differential along capillary, pounds per square foot
$\mu$ = viscosity of oil, pounds-second per square foot
$V$ = velocity of oil in capillary, feet per second
$L$ = length of capillary, feet
$D$ = inside diameter of capillary, feet.

In actual practice the tube is made slightly longer than the theoretical length needed to produce the desired pressure differential, the reason for this is that it is desired to have at least some energy input to the capillary heaters 16 even at the low end of the flow rate range. Thus, when the system is in operation, there will always be at least some heat input to the capillary in order to better maintain setpoint pressure. This strategy also precludes the need of using forced cooling to maintain set-point pressure. Dow Corning 200 Silicone ® Oil is especially useful in view of the variation of its viscosity with temperature, e.g., $\mu = 0.008$ lb-sec/ft$^2$ @90° F. and $\mu = 0.004$ lb-sec/ft$^2$ @160° F.

The method of the present invention involves the use of the present apparatus to measure the permeability and changes in permeability as a function of time of a solid, e.g. a geological formation extracted from the earth. Thus, the present invention is a method for determining the permeability and changes in permeability as a function of time of a solid, e.g., a geological formation in the form of a drilling core with the present apparatus by supplying a waste or test fluid to the fluid reservoir 11, applying sufficient pressure to the water side of the piston in the fluid reservoir by means of a pump 10 to pump the test fluid being transported to the solid holder 5 at a constant flow, e.g., in the range of from 6-600 ml/hr, maintaining a solid at a desired temperature and measuring that temperature as a function of time, maintaining sufficient pressure to the oil side of a piston in a receiver 14 thereby maintaining a desired pressure at 10 the discharge of the solid holder and selecting and measuring the rate at which fluid has passed through the solid and measuring the ΔP across the solid holder so that the permeability of the solid can be calculated.

The permeability can be determined by using the equation $$K = \frac{\mu \, Q \, L}{A \, \Delta P}$$

where
K = permeability in darcys
μ = viscosity of fluid flowing through the solid in centipoise
Q = volume flow rate flowing through the solid in milliliter/second
L = length of the solid sample in centimeters
A = cross-sectional area of the solid sample in centimeters squared
ΔP = pressure differential across the solid in atmospheres.

The plunger pump 10 is driven at a constant rate throughout any given test for the entire test. It is important that the test fluid be pumped at a constant rate through the test solid. The system pressure at which it is desired to operate is preselected and is effected by dialling in a set point on the control 26; thus, contingent on the output of transducer 17, the control 26 activates the electric heaters 16, the effect of which is to lower the viscosity of the oil in the capillary tube 15 thereby decreasing capillary tube pressure drop to maintain set-point pressure at the preselected level.

A core is removed from the earth by means of a hollow drill having an inside diameter of 3.5 inches. The test solid is then obtained from this 3.5 inch core by means of a hollow drill having 1.75 inches inside diameter by drilling along an axis at right angles to that of the 3.5 inch core thus obtaining a cylindrical core with a diameter of 1.75 inches. This is necessary in order that the test fluid flow through the solid in the same way it will flow through the earth strata, i.e., radially out from the bore hole. This cylinder is cut transversely to a length slightly (say 0.25 inch) in excess of the desired test solid length of 2 inches after which the core is "potted" on its circular perimeter only using a mold. In use the mold assembly is placed on its end on a table, then the 1.75 inch diameter solid is placed concentrically in the mold body aperture (which has a diameter of 2.5 inches), being supported by one or more two-inch long spacers contingent on the length of the solid; the upper end of the solid must protrude slightly (say 0.25 inch) above the end of the mold body. With the test solid in place in the mold, liquid epoxy resin is poured into the annular space surrounding the solid and is left to cure or harden forming jacket 40 (FIG. 2); an inwardly extending ring or flange inside the upper end of the mold body produces an annular groove around the perimeter of the epoxy resin which groove is for the O-ring 41 seen in FIG. 2. The mold used is made in two halves, secured by machine screws, and is disassembled to remove the jacketed solid which is machined on its upper end to smooth the rough, ascast epoxy surface and to reduce the solid and the jacket to its intended length (e.g., multiples of 2.0 inches). The unitary assembly of solid and jacket may now be placed in the apparatus of FIG. 2.

EXAMPLES 1-10—Best Mode

A 3.5 inch diameter earthen core was obtained by drilling in the vicinity of DeLisle, Mississippi to a depth of about 10,000 feet into the Washita-Fredricksburg formation which occurs throughout the southern portion of the North American continent. This formation comprises essentially sandstone; the 3.5 inch core was cross-drilled to obtain a 1.75 inch diameter core which was prepared and potted in epoxy as described above.

The apparatus described in FIG. 1 was used to measure the permeability of the core by the following procedure:

Referring now to FIG. 1, the thus prepared test core was placed in the solid or core holder 12, which was then closed, and the heating jacket 62 turned "on". Likewise, cooling water was admitted to cooling jacket 56.

Next, the oil pump 19 was operated, withdrawing Dow Corning 200 Silicone ® oil from sump 18, to completely fill tube 34, receiver 14, tube 24, pressure transducer 17 and capillary 15 via open valve 25. During this operation, the piston 32 of receiver 14 was driven downward approximately to the bottom of the receiver 14 the top of which became completely filled with oil. (If the apparatus had been used previously valve 33 may be opened to allow "spent" test fluid to flow out of the receiver via tube 35 after which valve 33 is closed again.) Valve 25 was next closed and the pump 19 was stopped.

Test fluid in tank 29 was charged into fluid reservoir 11, with pump 10 not operating, displacing piston 28 upward; valve 31 was closed on completion of charging. During this step, a valve (not shown) in tube 21 was closed to prevent test fluid from entering the core holder 12.

Control 26 was turned "on" to energize heater 16, heating capillary 15; a pressure set point was manually selected on control 26 to modulate the heat input to the capillary so that when oil flow occured it maintained a preselected pressure of the Silicone ® oil in tube 24 by means of pressure transducer 17.

The indicating and signal conditioning device 74 and the strip chart recorder 72 were energized.

The valve (not shown) in tube 21 was opened but test fluid did not flow until pump 10 was started. Pump 10 was started and its speed control (not shown) was manually set for a desired constant pump speed to provide constant delivery rate of water from sump 27 to the upper end of reservoir 11; this had the effect of driving piston 28 "down" forcing test fluid out at a constant flow rate via tube 21 to core holder 12 and to the test core 9. The capacity of reservoir 11 was 1 liter. Pump 10 can provide flow rates of 6-600 ml/hr at pressures up to 6000 psi. The time for one run can vary from 1.67-167 hours although typical run durations were 6.5 hours. Exiting the core, the test fluid entered receiver 14 below piston 32 driving it "up" and generating pressure in the Silicone ® oil thereabove. Oil pressure rose rapidly to the set point of control 26. Pressure was generated by the relatively large pressure drop induced across capillary 15 by the Silicone® oil which discharged at ambient atmospheric pressure.

The pump 10 is operated at constant speed or constant flow for a sufficiently long period to obtain a plot of ΔP across the test core on recorder 72. ΔP rose gradually as the test fluid interacted with the core material and as the test fluid tended to plug the core. The test fluid was maintained within 60°–80° F. temperature range until it contacted the core. The core temperature was also measured and recorded on recorder 72.

The following test fluid compositions were then passed through the core and the data summarized in the Table that follows:

(1) Brine: Dissolved the following reagent grade chemicals in tap water: 6 liters of tap water, 292 g of $CaCl_2.2H_2O$, 760 g of NaCl, 2.0 g of $Na_2SO_4$, 0.6 g of NaBr; filtered through diatomaceous earth.

(2) Acidizing Solution (10% HCl): Mixed 930 ml of tap water with 570 ml of HCl obtained from the waste stream of a plant manufacturing $TiO_2$ by the chloride process; filtered through diatomaceous earth before loading into the apparatus of the present invention.

(3) Stabilized Iron Chloride Waste Solution (hereinafter referred to as SICWS):
  (a) mixed 1800 ml of tap water, 2400 ml of HCl obtained from a waste stream of a plant manufacturing $TiO_2$ by the chloride process, and 3700 g of a solid discharge from a waste stream from the same plant.
  (b) stirred 10 minutes and added 12 ml of 5% Nalco 7120 solution and settled 48 hours.
  (c) decanted 5400 ml and stirred in 215 g of diatomaceous earth and filtered through filter paper.
  (d) this filtrate was polished filtered through a 30 g cake of diatomaceous earth yield 4000 ml of 1.338 S.G. test fluid.

SUMMARY OF DATA
Core: 1.75 in. diameter (15.52 Cm² cross-sectional area); 2 in. long (5.08 Cm) Taken by Drilling to a Depth od 9939 ft., Washita-Fredricksburg Formation, DeLisle. Mississippi

| Example | Test Fluid | Specific Gravity (20° C.) In | Out | Viscosity (cp) In | Out |
|---|---|---|---|---|---|
| 1 | Brine | 1.106 | 1.104 | 1.03 (35° C.) | 1.02 (35° C.) |
| 2 | 10% HCl | 1.048 | 1.057 | .90 (35° C.) | .89 (35° C.) |
| 3 | Brine | 1.104 | 1.102 | .99 (35° C.) | .98 (35° C.) |
| 4 | 10% HCl | 1.048 | 1.055 | .95 (35° C.) | .95 (35° C.) |
| 5 | SICWS | 1.318 | 1.230 | 1.91 (60° C.) | 1.24 (60° C.) |
| 6 | SICWS | 1.316 | 1.318 | 1.73 (60° C.) | 1.76 (60° C.) |
| 7 | SICWS | 1.320 | 1.318 | 1.81 (60° C.) | 1.72 (60° C.) |
| 8 | 10% HCl | 1.076 | 1.104 | .97 (35° C.) | 1.00 (35° C.) |
| 9 | Brine | 1.104 | 1.103 | 1.05 (35° C.) | 1.05 (35° C.) |
| 10 | Distilled Water | 1.000 | — | .72 (35° C.) | — |

| Example | Core Backpressure (psig) | Average Core Temperature (F.°) | Flow Rate (ml/sec) | Run Time (hrs) |
|---|---|---|---|---|
| 1 | 5000 | 92 | 0.043 | 6 |
| 2 | 5000 | 92.5 | 0.043 | 5 |
| 3 | 5000 | 100 | 0.043 | 7 |
| 4 | 5000 | 92 | 0.043 | 6.3 |
| 5 | 5000 | 138 | 0.043 | 1.5 |
| 6 | 5000 | 138 | 0.043 | 5 |
| 7 | 5000 | 138 | 0.043 | 3 |
| 8 | 5000 | 93 | 0.043 | 6.5 |
| 9 | 5000 | 92 | 0.043 | 6.5 |
| 10 | 5000 | 94 | 0.043 | 6.0 |

| Example | Permeability Range (md) | ΔP Increase Inches $H_2O$/hr | Final ΔP (in. $H_2O$) |
|---|---|---|---|
| 1 | 161→154 | 0.25 | 38 |
| 2 | 177 | 0 | 29 |
| 3 | 154 | 0 | 36.5 |
| 4 | 152 | 0 | 35.5 |
| 5 | 131→111 | 13 | 97.5 |
| 6 | 101→57 | 14 | 172.5 |
| 7 | 92→35 | 57 | 292.5 |
| 8 | 172 | 0 | 32.0 |
| 9 | 176→169 | .25 | 35.5 |
| 10 | 182→157 | .60 | 26.0 |

Calculation of Final Permeability for Example 9:
Flow Rate: 0.043 ml/sec
Final Core ΔP: 35.5 in. $H_2O$ = 0.0873 ATM
Final Fluid Viscosity: 1.05 cp $$K = \frac{\mu Q L}{A \Delta P} = \frac{1.05 \times 0.043 \times 5.08}{15.52 \times 0.0873} =$$
$$0.169 \text{ Darcy} = 169 \text{ md (millidarcy)}.$$

Example 1 involved passing brine through the core to establish a baseline permeability of 154 md.

Example 2 involved passing a 10% HCl through the core to simulate an acidization procedure.

Example 3 involved passing brine again through the core, a 154 md permeability was measured, equal to the baseline permeability, indicating HCl had not adversely effected the core.

Example 4 involved passing a 10% HCl through the core to simulate providing a buffer fluid in the well prior to waste fluid injection.

Examples 5, 6 and 7 involved passing a test fluid through the core ending with a core permeability to this fluid of 35 md. The relatively low final permeability of the core to this fluid in conjunction with the steady increase in core ΔP with time indicated that the test fluid had not been sufficiently stabilized.

Example 8 involved passing 10% HCl through the core to return its permeability to this fluid to 172 md, a value not significantly different from that measured in Example 2.

Example 9 involved passing brine through the core and obtaining a final permeability to this fluid of 169 md, a value not significantly different from the baseline permeability of 154 md indicating that the procedure to this point produced no irreversible effects in the core.

Example 10 involved passing distilled water to the core and obtaining a final permeability to this fluid of 157 md.

The apparatus of this invention is useful in carrying out under controlled and predetermined conditions the flow of fluids through porous materials actually taken from geological deposits in the earth. Numerous tests and results are thereby easily made available so that the effect, e.g., of the disposal of waste fluids in any given location can be predicted as well as the permeability of various materials for determinations applicable to entirely different operations.

The method of the invention provides a convenient and easy method of determining the permeability and the chemical interaction of fluids with respect to samples of geological deposits taken from the earth. The present method permits measurement at constant flow and constant pressure at the core exit for periods of up to 167 hours automatically with the size apparatus used in the present examples. However, the length of runs can be increased by simply increasing the receiver size as well as by adjusting other capacities.

I claim:

1. An apparatus for determining the permeability and changes in permeability to fluids as a function of time of a solid at a particular temperature and pressure and flow rate, said apparatus comprising a precision plunger-type pump, means for controlling the flow rate of liquid from the pump, a fluid reservoir housing a movable piston that divides the interior of the reservoir into two sides, a fluid side and a test fluid side, said pump connected to the fluid side of the fluid reservoir to permit said piston to be actuated by the fluid pressure exerted on the movable piston of the reservoir by the pump, a solid or core holder with an inlet and exit means, the test fluid side of the reservoir connected to an inlet connection for the solid holder, a heater adjacent to the solid holder with means for maintaining a solid in the solid holder at any temperature, a differential pressure transducer, the transducer is connected to the entrance and exit means for the solid holder to measure and record differential pressure continuously as a function of time, a receiver with a movable piston housed therein that divides the interior of the receiver into two sides, a test fluid side and an oil side, means for passage of the test fluid from the reservoir to the inlet of the solid holder, means for passage of the test fluid from the exit of the solid holder to the test fluid side of the receiver, a pressure transducer, a pressure let-down capillary connected through the pressure transducer to the oil side of the receiver, a heater adjacent to the pressure let-down capillary for heating the oil in the capillary, means for connecting to said pressure transducer and said heater for controlling the heat provided by the heater to permit a constant pressure downstream of the solid holder by providing a controlled pressure to the receiver piston to control the exit pressure of the fluid from the solid holder.

2. The apparatus of claim 1 wherein the test fluid is provided with a cooling means immediately prior to entering the solid to prevent appreciable heat-up of the test fluid before it reaches the solid.

3. A method for determining the permeability and changes in permeability as a function of time of a solid with the apparatus of claim 2 which comprises pumping a test fluid through the solid confined in said apparatus at a substantially constant flow rate, maintaining the test fluid at substantially constant temperature until it reaches the solid, maintaining a constant pressure of test fluid downstream of the solid and measuring the $\Delta P$ across the solid as a function of time.

4. The method of claim 3 wherein the constant pressure downstream of the solid is 3000–40,000 psig.

5. The apparatus of claim 1 having a means for measuring and recording temperature as a function of time at the solid holder.

6. The apparatus of claim 5 wherein the test fluid is provided with a cooling means immediately prior to entering the solid to prevent appreciable heat-up of the test fluid before it reaches the solid.

7. A method for determining the permeability and changes in permeability as a function of time of a solid with the apparatus of claim 6 which comprises pumping a test fluid through the solid confined in said apparatus at a substantially constant flow rate, maintaining a constant pressure of test fluid downstream of the solid and measuring the $\Delta p$ across the solid as a function of time.

8. A method for determining the permeability and changes in permeability as a function of time of a solid with the apparatus of claim 5 which comprises pumping a test fluid through the solid confined in said apparatus at a substantially constant flow rate, maintaining a constant pressure of test fluid downstream of the solid and measuring the $\Delta P$ across the solid as a function of time.

9. A method for determining the permeability and changes in permeability as a function of time of a solid with the apparatus of claim 1 which comprises pumping a test fluid through the solid confined in said apparatus at a substantially constant flow rate, maintaining a constant pressure of test fluid downstream of the solid and measuring the $\Delta P$ across the solid as a function with time.

10. The method of claim 9 wherein the constant pressure downstream of the solid is 3000–40,000 psig.

* * * * *